United States Patent [19]

Roper

[11] 4,198,621

[45] Apr. 15, 1980

[54] ELECTRICAL REMOTE SENSING SYSTEM

[75] Inventor: Graham B. Roper, Newbury, England

[73] Assignee: Crowcon (Instruments) Limited, England

[21] Appl. No.: 850,945

[22] Filed: Nov. 14, 1977

[51] Int. Cl.² ............................................. G08C 19/16
[52] U.S. Cl. ........................................ 340/210; 340/206; 340/207 R
[58] Field of Search ............... 340/206, 207, 310 A, 340/210; 323/DIG. 1

[56] References Cited

U.S. PATENT DOCUMENTS

| | | | |
|---|---|---|---|
| 3,717,858 | 2/1973 | Hadden | 340/203 |
| 3,733,540 | 5/1973 | Hawkins | 321/47 |
| 3,818,306 | 6/1974 | Marini | 321/2 |
| 3,906,437 | 9/1975 | Brandwein | 340/27 |
| 4,016,480 | 4/1975 | Hoffman | 323/8 |
| 4,095,165 | 6/1978 | Boros | 323/DIG. 1 |

FOREIGN PATENT DOCUMENTS 2445337  4/1976  Fed. Rep. of Germany ........... 340/210

*Primary Examiner*—Gareth D. Shaw
*Assistant Examiner*—Joel Miller
*Attorney, Agent, or Firm*—Leydig, Voit, Osann, Mayer & Holt, Ltd.

[57] ABSTRACT

A sensing unit described in which the cable providing the unit with power also acts to transmit a signal representative of the parameter being sensed e.g. gas concentration. The unit comprises a switched mode voltage regulator the switching frequency of which corresponds to the value of the parameter being sensed.

7 Claims, 3 Drawing Figures

ELECTRICAL REMOTE SENSING SYSTEM

FIELD OF THE INVENTION

This invention relates to remote sensing using electrically powered sensors.

BACKGROUND TO THE INVENTION

There are many applications in which it is desired to monitor a condition at a remote location. Examples include measuring temperature, pressure, humidity, gas concentration, flow rate and mechanical stresses in meteorology, civil engineering, mining, oil refining, natural gas and oil production and others.

By far the most satisfactory method of monitoring conditions at remote locations is to position at the remote location an electrically driven sensor unit which is provided with means to transmit to a central location a signal representative of the parameter in question. The signal may be transmitted by wireless communication, but it is generally simpler and less expensive to transmit by cable. The provision of a cable between the central monitoring station and individual sensors also enables the sensors to be driven from power supplied from a central unit rather than needing each to be supplied with its own power generation or storage system.

Detector and sensor units are often dependent for their accuracy on a stabilised power supply. This gives rise to difficulties particularly where long cable runs are involved since these are subject to voltage drop and other fluctuations and it is frequently necessary to provide an individual stabilising unit at each remote location.

Conventional series regulators are very inefficient, particularly when designed to operate over a large input voltage range. This power loss may make system design difficult or impossible in cases where the inherent power consumption of the sensor device is not much less than the maximum power which may be transmitted through the protective zener barriers which are fitted to the supply lines of electrical equipment used in hazardous areas. In such cases, it may be desirable or even essential to use an efficient voltage regulator of the "switched mode" type. Switched mode voltage regulators, often referred to simply as "switching regulators" are described in, e.g. R. S. Olla "Switching regulators: the efficient way to Power" Electronics, 16th Aug. 1973 at page 91 ff.

In systems of this kind, it is desirable, for economic reasons, that the cable carries both power and signal from the sensor to the central unit. Variable frequency signalling over a frequency range of e.g. 10 to 20 kHz or higher constitutes an acceptable and widely used system, but if this is combined with switched mode voltage regulators interference may be caused by harmonics of the basic stabiliser frequency transmitted on the cable. These disadvantages can in some cases be overcome by sophisticated filtering techniques but such techniques are themselves bulky and expensive.

GENERAL DESCRIPTION OF THE INVENTION

According to the present invention there is provided a sensing unit for monitoring a parameter at a remote location and adapted to be connected by a power supply and signal carrying cable to a central location, which unit comprises a sensor element, means for converting the condition of the sensor element to a variable frequency signal representative of a variable parameter at the remote location and a switched mode voltage regulator connected to the power and signal carrying cable to provide a stable power source for the sensing unit, the switching frequency of the switched mode voltage regulator being identical to and varying in dependence on the variable frequency signal representative of the value of the parameter.

Such sensing unit may easily be constructed compactly and merely requires connecting to a central power source by means of an appropriate cable. The cable may be fed with a direct current supply and the operation of the switched mode voltage regulator will give rise to ripple generation on the supply voltage which can be detected back at the central station. The frequency at which the regulator operates at any given moment will be dependent on the value of the parameter which the sensing unit is designed to monitor and can accordingly be used in known fashion to give an indication of the value of the parameter at the remote location at any time. Overtones and harmonics of the ripple frequency on the power supply line may be suppressed to any desired level or eliminated by connecting a capacitor of appropriate value across the line at its end adjacent to the sensing unit.

The individual components of the circuitry should be so chosen as to match the desired frequency range corresponding to variation in the parameter being monitored with the area of optimum efficiency of the switched mode voltage regulator. By careful component choice it is possible to use regulators having an efficiency of 80 or even 90% over a wide range of applied input voltages.

The combination of a switched mode voltage regulator circuit with variable frequency tone telemetry gives rise to considerable advantages. Sensing units according to the invention may operate efficiently over a wide range of supply voltages and accordingly can be used without too much difficulty even at widely varying distances from a single central power supply source. A single twin conductor cable is all that is required both to transmit the operating power and return the variable frequency signal representative of the parameter being monitored. Because it is the frequency of the ripple voltage which is observed, measurement errors due to voltage drop or other losses do not arise.

The overall power consumed by sensing units according to embodiments of the present invention may be low and it is to be noted in particular that switched mode voltage regulator circuits have very little heat dissipation on account of their high efficiency; this makes the sensor unit of particular value in mines, explosive gas environments and the like. Furthermore the sensing units embodying the present invention are simple and substantially free of complex or sophisticated filtering devices.

A plurality of sensing units according to the present invention may be connected to a single central control and monitoring unit. Such a central unit may comprise means for scanning the plurality of sensing units connected thereto, and for providing a real time display representative of the values of the parameters at the locating of the sensing unit. Such overall systems are particularly useful when monitoring complex systems such as off shore oil production platforms or oil prospecting rigs.

DESCRIPTION OF PREFERRED EMBODIMENT

By way of example, the accompanying drawings illustrate a particular sensor according to the invention. In the drawings.

Figure 1:
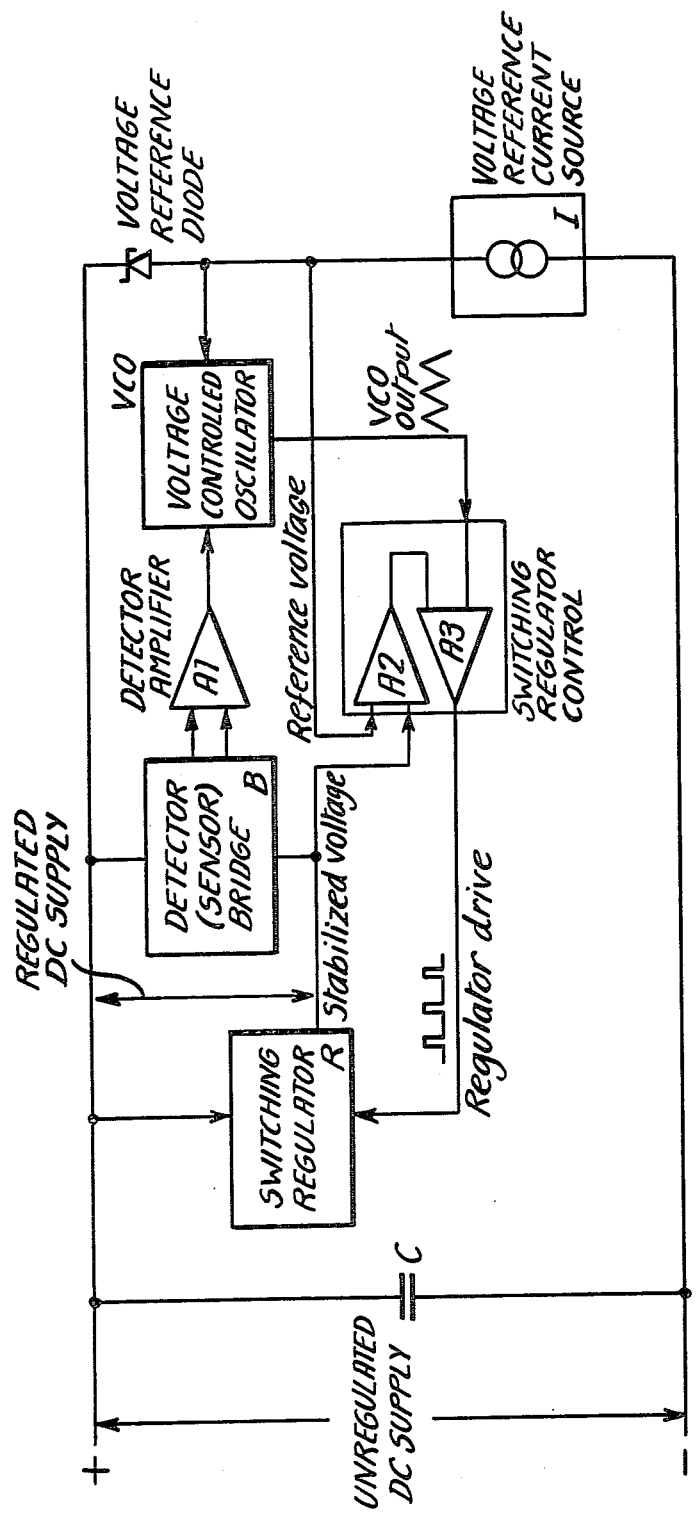
FIG. 1 is a block diagram of a detector head.

In FIG. 1, a conventional switched mode voltage regulator R is driven by the 'on-off' drive waveform from a comparator A3. The stabilised output from this regulator supplies the detector (sensor) itself, B, and may also be used to supply other electronic circuitry if required.

The detector output is amplified by a detector amplifier A1 to a level suitable for driving the frequency control input of a voltage-controlled oscillator (VCO) over the desired output frequency range.

A reference diode D is fed from a conventional constant-current source, I, to give a reference voltage that is substantially independent of the unregulated DC supply voltage over the design operating range. This reference voltage, or a fixed fraction of it, is applied to one input of the differential amplifier A2, and compared with the switching regulator output voltage, which is applied to the other input of A2. In order to ensure that the circuit is self-starting on switch-on, the VCO is also supplied from the reference voltage (the VCO is preferably a complementary-MOS integrated circuit, which draws so little supply current that it imposes negligible loading on the reference voltage rail).

The output from A2, (which is a DC voltage the value of which depends on the difference between the reference voltage and the stabilised output of the switched mode voltage regulator), feeds one input of a comparator A3. The other input is a triangular waveform derived from the VCO—the output of A3 is a digital (on-off) waveform at the VCO frequency, but having a mark-space ratio which depends on the relative levels of A2 output and the triangular waveform.

This variable mark-space ratio waveform is applied as drive to the switched mode voltage regulator. Over the design VCO frequency range, the stabilised output from the switched mode voltage regulator depends only on the drive mark-space ratio, and is independent of frequency. The loop formed by the switched mode voltage regulator, A2 and A3 thus acts to hold the switched mode voltage regulator stabilised output constant, while the VCO frequency is varied in accordance with the detector (sensor) output.

The switched mode voltage regulator draws current in a series of pulses (at the VCO frequency) from the unregulated DC supply terminals. This supply is decoupled by the capacitor C which partially discharges while the switched mode voltage regulator is drawing current, and charges up again via the unregulated DC supply impedance while the switching regulator is 'off'. This action results in a 'sawtooth' voltage at the VCO frequency appearing across capacitor C—its amplitude may be controlled by suitable choice of capacitance of capacitor C, and the VCO frequency may be determined by the central monitoring station at the remote end of the power supply cable by circuitry which detects either the alternating voltage or the current component on the supply line.

Figure 2:
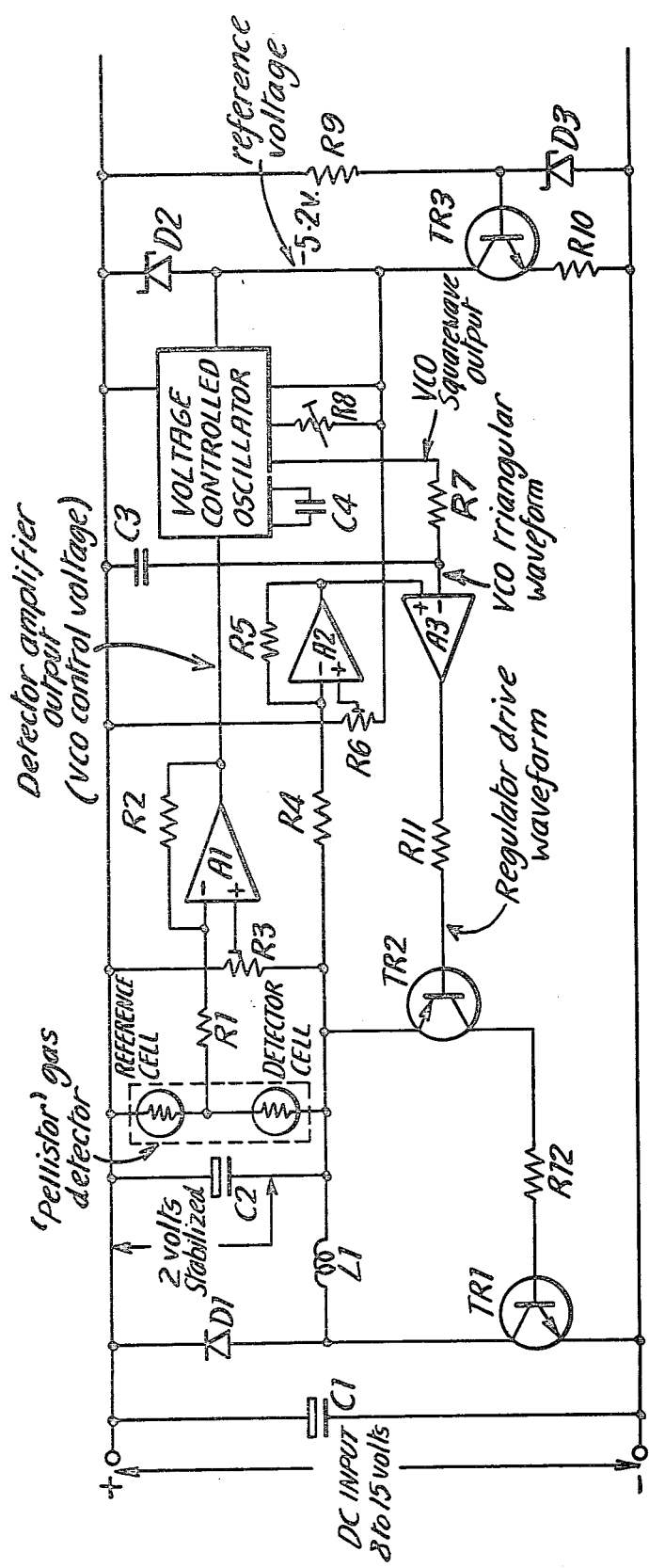
FIG. 2 is a skeleton circuit diagram of the detector head of FIG. 1.

In the skeleton circuit diagram of FIG. 2, the switched mode regulator is formed by transistor TR1, diode D1, inductor L1 and capacitor C2. This particular circuit represents a device using a 'pellistor' type of flammable gas detector (see Mining Engineering Jan. 1969 p. 237-244). The pellistor sensor is used in a bridge circuit which requries a stabilised supply at about 2 volts, 200 mA DC. The bridge is formed by the 'reference' and 'detector' cells as shown, and the resistor R3, and is supplied from the 2 volt supply developed across C2.

The bridge output is amplified by A1 (whose gain is determined by R1 and R2) to a suitable level to drive the VCO. In this design, the VCO normally operates, when the detector bridge is balanced, at 20 KHz, as determined by the values of C4 and R8 and the control voltage from A1. When the presence of a flammable gas or vapour unbalances the bridge, the output of A1 moves in such a direction as to reduce the VCO frequency, until at a gas level of 100% of full scale, the VCO frequency is 10 KHz.

The output from the particular integrated circuit used as the VCO is a squarewave—this is integrated by the components R7 and C3 to produce a triangular wave at the inverting input of A3. The action of the error amplifier A2 and the comparator A3 are as previously described. The variable mark-space ratio output from A3 is amplified by TR2 to a suitable level to drive the switching transistor TR1.

It is necessary to ensure that adequate base drive is available for TR1 fully to saturate a worst-case (low current gain) transistor, at the lowest required unregulated DC supply voltage, and R12 is chosen accordingly. At higher supply voltages, the voltage across R12 rises, and there is therefore considerable excess base drive. In order to avoid wasting this current and thus reducing the efficiency of the regulator, TR2 emitter is returned to the stabilised rail rather than the positive supply rail—the TR1 base drive current thus contributes to the load current drawn by the detector bridge.

The zener diode D2 is fed from the constant-current supply formed by TR3, D3, R9 and R10, and thus provides the stable reference voltage. A fraction of this voltage, determined by the setting of R6, is compared with the switched mode voltage regulator output voltage in A2 as previously described. R6 is adjusted, in this circuit, to give 2 volts across the detector bridge.

The value of capacitor C1 is chosen so as to result in a component of supply voltage or current ripple which is adequate for detection, with a suitable margin of safety, at the remote 'central monitoring station' end of the cable over which the detector head unit is powered.

Figure 3:
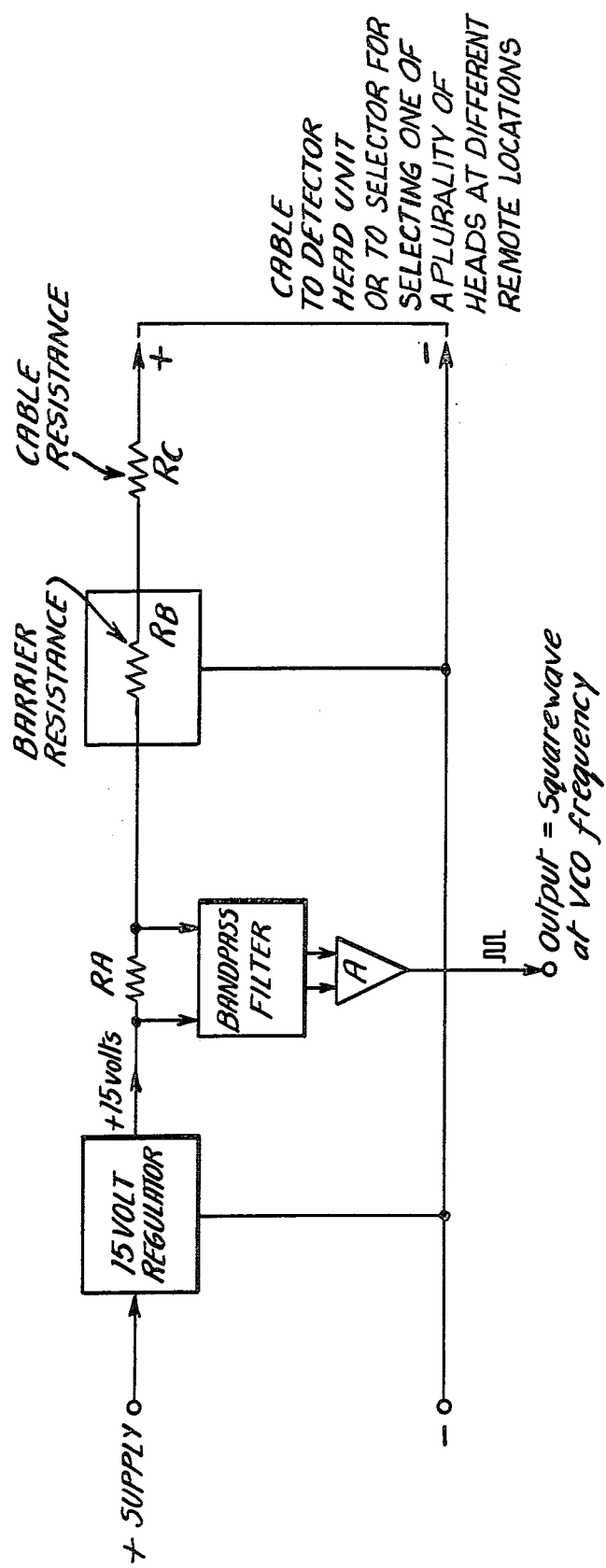
FIG. 3 is a skeleton circuit diagram of a central monitoring station which can be arranged to monitor a number of detector heads according to FIGS. 1 and 2.

In the central monitoring station skeleton circuit diagram, FIG. 3, a conventional voltage regulator provides a regulated DC supply to the cable feeding the Detector Unit described above. This supply is fed via the resistor RA, the total resistance RB of any zener barrier that may be fitted for safety purposes if the Detector Head is installed in a hazardous area, and the cable resistance, RC. Since RA and RB, (if fitted) are subject to normal tolerances, and RC is a variable dependent on cable size, length and temperature, the cable voltage at the Detector Head unit is effectively unregulated, within the permitted limits.

The voltage developed across RA contains a ripple component at the Detector Head VCO frequency due to the ripple current flowing in the cable as a result of the switched mode voltage regulator action, as described above. This is filtered by the band pass filter, to attenuate unwanted noise or interference components outside the expected range of frequencies, and applied to the comparator A. The output from the comparator is a squarewave at the Detector Head Unit VCO frequency, and this is processed by conventional digital circuitry to extract the frequency and hence Detector Head gas level.

The comparator A is provided with some hysteresis in order to establish a threshold signal level below which no output will be obtained. Thus, if the Detector Head Unit should fail or the cable become damaged so that the normal ripple amplitude is no longer present then the comparator A will produce no output, which will be interpreted by the following circuitry as a fault condition.

The central monitoring station of FIG. 3 may be connected to scan each of a plurality of sensing units by known means.

I claim:

1. A sensing unit for monitoring a parameter at a remote location and adapted to be connected by a power supply and signal carrying cable to a central location, the unit consisting essentially of a sensor element having an electrical condition varying in dependence on the value of the parameter, means connected to the sensor element for converting the condition of the sensor element to a variable frequency signal representative of a variable parameter at the remote location, and a switched mode voltage regulator arranged to operate at a switching frequency, connected to the power and signal carrying cable and to the converting means and arranged to provide a stable fixed voltage power source forming part of the sensing unit, wherein the switching frequency of the switched mode voltage regulator is identical to and continuously varying in dependence on the variable frequency signal representative of the value of the parameter, while the regulator maintains the voltage applied to the converting means at a fixed value.

2. The sensing unit of claim 1 and further including a capacitor across the power supply and signal carrying cable at least to attenuate overtones and harmonics.

3. The sensing unit of claim 1 including means to produce a train of pulses having a variable mark space ratio and wherein the switched mode voltage regulator produces a voltage dependent upon the mark space ratio of the train of pulses fed thereinto.

4. The sensing unit of claim 1 wherein the sensor element is an electrical bridge element.

5. The sensing unit of claim 1 wherein the sensor element is adapted to detect gas concentration.

6. A control and monitoring system comprising a plurality of sensing units according to claim 1 and means for connecting each unit to a central control and monitoring unit.

7. The system of claim 6 wherein the central unit comprises means for scanning a plurality of sensing units connected thereto and for providing a real time display representative of the values of the parameters at the locations of the sensing units.

* * * * *